United States Patent [19]

Law et al.

[11] Patent Number: 5,622,825
[45] Date of Patent: Apr. 22, 1997

[54] EFFICIENT GENE PROBE CONJUGATIONS BY AN UNCONVENTIONAL MIXED ANHYDRIDE METHOD

[75] Inventors: Say-Jong Law, Westwood; Hana Lukinsky, Mansfield, both of Mass.

[73] Assignee: Ciba Corning Diagnostics Corp., Medfield, Mass.

[21] Appl. No.: 358,963

[22] Filed: Dec. 19, 1994

Related U.S. Application Data

[63] Continuation of Ser. No. 775,399, Oct. 16, 1991, abandoned.
[51] Int. Cl.$^6$ .............................. C12Q 1/68; C12P 19/34; C07H 21/04; C12N 15/00
[52] U.S. Cl. .......................... 435/6; 435/91.1; 435/879; 435/968; 536/23.1; 536/24.3; 536/24.32; 536/25.32; 935/5; 935/8; 935/76; 935/77; 935/78
[58] Field of Search ............................ 435/6, 968, 91.1, 435/879; 935/77, 78, 5, 8, 76; 536/25.32, 24.32, 25.3, 23.1, 24.3

[56] References Cited

U.S. PATENT DOCUMENTS 4,745,181  5/1988  Law et al. .............................. 530/387

OTHER PUBLICATIONS

Agrawal, S. et al, Efficient Methods for Attaching Non-Radioactive Labels to the 5' Ends of Synthetic Oligodeoxyribonucleotides, Nucleic Acids Res., 14 (1986) 6227.
Chollet, A. et a, Biotin–Labeled Synthetic Oligodeoxyribonucleotides: Chemical Synthesis and Uses as Hybridization Probes, Nucleic Acids Res., 13(1985) 1529.
Clontech Laboratories, Inc., DNA Modification Reagents For Use in Automated DNA Synthesis, 1989.
Schroeder, H. R. et al, Monitoring Specific Protein–Binding Reactions with Chemiluminescence, Methods in Enzymology, 57(1978) 424.
STN, Registry file, RN 82029–66–1, sequence (nucleotide) comparison with probe SYOMPA 480.24.

*Primary Examiner*—W. Gary Jones
*Assistant Examiner*—Bradley L. Sisson
*Attorney, Agent, or Firm*—Arthur S. Morgenstern; Judith A. Roesler

[57] ABSTRACT

A novel method for conjugating haptens, ligands or luminescent labels to polynucleotides has been developed. This method involves the formation of a mixed anhydride, followed by reaction of the mixed anhydride intermediate with a nucleophilic group-containing polynucleotide in a DMF/water solvent system. The resulting compound finds usefulness especially in the gene probe area.

20 Claims, 1 Drawing Sheet

GENE PROBE SANDWICH ASSAY CONFIGURATIONS

GENE PROBE SANDWICH ASSAY CONFIGURATIONS

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 27 bases
( B ) TYPE: nucleic acid
( C ) STRANDEDNESS: single
( D ) TOPOLOGY: linear ( x i ) SEQUENCE DESCRIPTION: SEQ ID NO:1:

GTA CCG TCA GAA TTC TTC CCT AAG AAA       27

( 2 ) INFORMATION FOR SEQ ID NO:2:

( i ) SEQUENCE CHARACTERISTICS:
( A ) LENGTH: 24 bases
( B ) TYPE: nucleic acid
( C ) STRANDEDNESS: single (D) TOPOLOGY: linear (xi) SEQUENCE DESCRIPTION: SEQ ID NO:2:

AAA GCT CAG GGC GTT CAG TTG ACC    24

(2) INFORMATION FOR SEQ ID NO:3:

(i) SEQUENCE CHARACTERISTICS:
      (A) LENGTH: 31 bases
      (B) TYPE: nucleic acid
      (C) STRANDEDNESS: single
      (D) TOPOLOGY: linear (xi) SEQUENCE DESCRIPTION: SEQ ID NO:3:

TCT GCC TCT CCC TCA CTC TAG ACT ATG AGT T    31

(2) INFORMATION FOR SEQ ID NO:4:

(i) SEQUENCE CHARACTERISTICS:
      (A) LENGTH: 27 bases
      (B) TYPE: nucleic acid
      (C) STRANDEDNESS: single
      (D) TOPOLOGY: linear (xi) SEQUENCE DESCRIPTION: SEQ ID NO:4:

GCC TTC GCA ATG GGT ATT CTT GGT GAT    27

(2) INFORMATION FOR SEQ ID NO:5:

(i) SEQUENCE CHARACTERISTICS:
      (A) LENGTH: 27 bases
      (B) TYPE: nucleic acid
      (C) STRANDEDNESS: single
      (D) TOPOLOGY: linear (xi) SEQUENCE DESCRIPTION: SEQ ID NO:5:

TGT TAG CAA CTA AAT ACG TGG GTT GCG    27

EFFICIENT GENE PROBE CONJUGATIONS BY AN UNCONVENTIONAL MIXED ANHYDRIDE METHOD

This is a continuation of application Ser. No. 07/775,399 filed on Oct. 16, 1991, now abandoned.

BACKGROUND OF THE INVENTION

Gene probes are important in the medical diagnostic area. The identification of genetic material in an organism can help to predict the predisposition of that organism to certain diseases. In addition, the identification of genetic material from infectious organisms can help to pinpoint the causation of diseases.

The gene probe area has been developing for several years, and its technical and popular literature has been prolific. See, for example, Klausner et al, *Bio/Technology*, Aug., 1983, p. 471; Bylinsky, *Fortune*, Jul. 9, 1984, p. 140; Engleberg, *ASM News*, Vol. 57, No. 4, 1991, p. 183; Gillespie, *Veterinary Microbiology*, 24 (1990) 217.

In gene probe assays, one of the key reagents utilized is the nucleic acid probe conjugated to an active molecular species. A nucleic acid probe is a single-stranded nucleic acid sequence that will combine (anneal) with a complementary single-stranded target nucleic acid sequence to form a double-stranded molecule (hybrid). The probe can either be totally synthetic, or from a biological source (recombinant DNA), or some combination of the two.

The active molecular species (also referred to as labels) can include such things as hapten, ligand or luminescent label. A hapten is an incomplete antigen, incapable by itself to provoke an immune response but, when suitably attached to another molecule, becomes capable of producing antibodies which will specifically recognize the hapten. A ligand is any compound for which a receptor naturally exists or can be prepared. A receptor is any compound capable of recognizing a particular spatial and polar organization of a molecule, i.e., epitopic site. Illustrative receptors include antibodies, enzymes, antibody fragments (such as Fab fragments), lectins, complement components, rheumatoid factors, hormones, avidin, staphylococcal protein A, and the like. Luminescent labels include such things as organic chemicals, organic metal chelate complexes or biopolymers capable of emitting light of longer wavelengths upon being excited with various sources of energy, introduced either in the form of light of shorter wavelengths (fluorescence) or derived internally from the molecule itself as a result of chemical conversion (chemiluminescence).

In some assays, for example in a sandwich-formatted assay, two kinds of nucleic acid probe conjugates (capturing probe and signalling probe) can be utilized. The main function of hapten or ligand in the capturing probe is to mediate the capturing of hybridized (annealed) nucleic acids (consisting of the target nucleic acid and the capture probe) by complexing with the anti-hapten IgG or the receptor immobilized on a solid phase. Through hybridizing to the neighboring region of the target nucleic acid, signalling probe facilitates the detection of the sandwich hybrid by virtue of its incorporated signal label that either is capable of signal producing or can be specifically bound to a binding protein which in turn carries or is capable of producing amplified signals. An amplified signal can be exemplified by a biotin/avidin system. Avidin, being a large molecule, can be reacted with several acridinium ester groups, so that the resulting modified avidin molecule has a much greater signal than if only one acridinium ester was present. Thus an "amplified" signal is obtained. A further example of a binding protein carrying an amplified signal is the receptor/liposome system. Liposome, being a cell-mimicing vescicle, can encapsulate thousands of suitably modified acridinium esters (hydrophilic acridinium esters) or other luminescent compounds and be subsequently attached to a number of receptors on its outer surface by covalent linkages. (See copending patent application Ser. No. 07/226,639, filed Aug. 1, 1998, abandoned in favor of file-wrapper-continuation application Ser. No. 07/826,186, filed Jan. 22, 1992, now U.S. Pat. No. 5,227,489, issued Jul. 13, 1993.) Examples of both capturing and signal probes are shown in FIGS. 1 and 2.

The type of signal is not critical for our purposes and can include radioactive, luminescent, phosphorescent, and other types of signals, for example the use of acridinium esters, phycobiliproteins, and the indirect biotin-avidin, or alkaline phosphatase systems.

Many techniques for coupling the probes with active molecular species are known. These include (1) modifying the purine or pyrimidine moiety of the nucleotide or (2) attaching certain functional groups to the 5'- or 3'- ends of the probe. Even though the latter approach of functionalizing the 5'- or 3'- ends of nucleic acids is generally preferred because interference between the probes and target nucleic acids can be minimized, the techniques herein can also be utilized to modify the individual prederivatized bases of the polynucleotides.

Synthesis of polynucleotides of even more than 100 bases in length has become common practice since the commercialization of DNA synthesizers, which employ, among other techniques, the phosphoramidite coupling chemistry. Several techniques of functionalizing probes at the 5'- or 3'- ends have been reported. Agrawal et al [*Nucleic Acid Res.*, 14 (1986) 6227] attached a ribonucleoside to the 5'- end of the deoxyoligonucleotide, oxidizing the ribosyl moiety with periodate to generate the functional groups of dialdehyde for coupling. Furthermore, a series of deoxyoligonucleotide modifiers containing homologous aminoalkyl or mercaptoalkyl groups have been made commercially available (e.g., by Clontech Laboratories, Inc., Palo Alto, Calif.). These can be added wherever desired (3'- end, middle of the oligomer chain, or 5'- end) during preparing the oligonucleotides on an automated synthesizer.

When an aminoalkyl-functionalized probe is selected for coupling, ligands carrying a variety of functional groups can be utilized to form stable conjugates. For example, the use of fluorescein with isothiocyanate (FITC), an already activated form of ligand, has been reported in Nucleic Acid Res., Vol. 13 (1985) 1529. The use of biotin with carboxylate, reported in Nucleic Acid Res., Vol. 14 (1986) 6227, requires preactivation with N-hydroxysuccinimide (NHS) to form biotin-NHS. However, in both cases, vast excess of ligands, exceeding a molar ratio of 500:1, were needed to drive the reaction and to maximize the usage of synthetic oligonucleotide. The adoption of such a high loading ratio has been widespread among those who practice this coupling chemistry and is believed to be necessary because of the aqueous lability and/or mild reactivity of these two activation forms. The yield of probe conjugate from these reactions is reasonably high (greater than 80%). However, the disadvantages are those associated with use of large excesses of one reactant, namely tedious work-up, difficult purification, and cost.

SUMMARY OF THE INVENTION

A novel method for conjugating haptens, ligands or luminescent labels to polynucleotides has been developed. This method involves the formation of a mixed anhydride, followed by reaction of the mixed anhydride intermediate with a nucleophilic group-containing polynucleotide in a DMF/water solvent system. The resulting compound finds usefulness especially in the gene probe area.

DETAILED DESCRIPTION OF THE INVENTION

Figure 1:
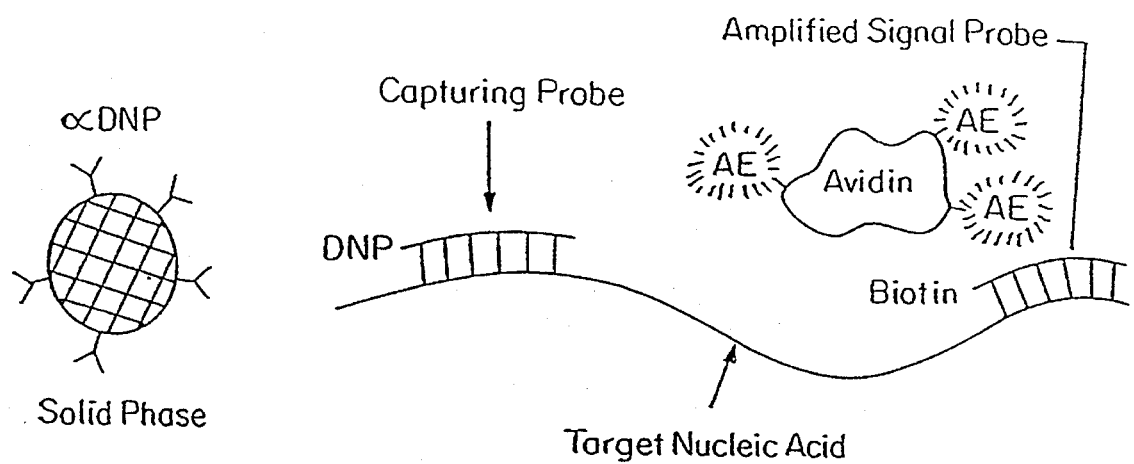
FIGS. 1 and 2 shows several gene probe sandwich assay configurations with both capturing and signalling probes.
Figure 2:
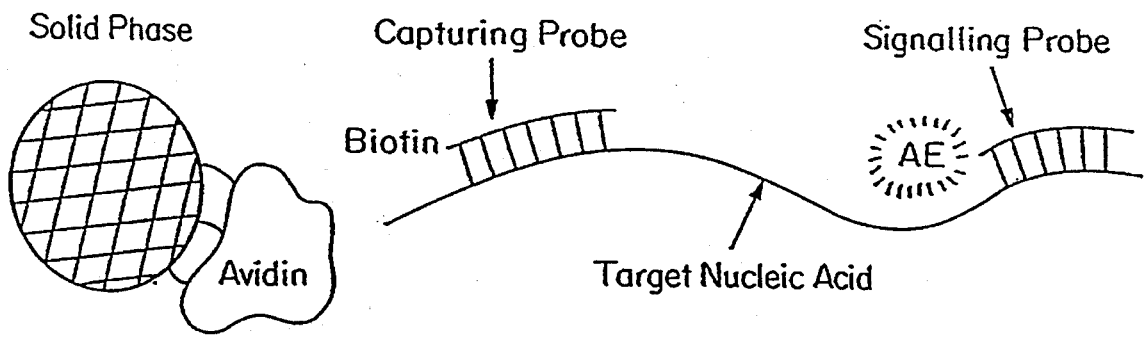

A technique for reacting a compound containing a carboxylate group with a compound containing an amino or sulfhydryl group to form a stable amide or the less stable thioester linkage is well known in organic chemistry. One common method of activating carboxylate group is to prepare a mixed anhydride derivative in nonaqueous media. The technique involves the activation of the carboxylate group with an alkyl chloroformate or aryl chloroformate to form a reactive mixed anhydride intermediate, which further reacts with the amino or sulfhydryl group of the second compound to form a conjugate. See, for example, Schroeder et al, Methods in Enzymology, Vol. 57 (1978) p. 424, which reported the preparation of a thyroxine-isoluminol conjugate by a mixed anhydride method using anhydrous organic solvent mixture as the solvent. Law (copending application Ser. No. 07/094,667, filed Sep. 9, 1987, abandoned in favor of file-wrapper-continuation application Ser. No. 07/954,606, filed Sep. 30, 1992, abandoned; see EP application 88308254.7, published Mar. 15, 1989, for equivalent European application.) utilized this technique in an anhydrous chloroform/DMF mixture to prepare a thyroxin-succinate-phosphatidylethanolamine conjugate. Aqueous environment is avoided because of the high reactivity and sensitivity of the mixed anhydride intermediate to moisture and because of the possibility of side reactions occurring on the purine or pyrimidine rings of the nucleotide, thus hindering hybridization.

Unexpectedly, it was found that, under well-chosen conditions, ligands activated by the mixed anhydride method can react well with the aminoalkyl-functionalized oligonucleotide in dimethylformamide (DMF)/water mixtures giving comparable yield of probe conjugates at a much lower loading ratio of 20:1.

The reaction scheme involved the activation of the carboxylate-containing ligands with an alkyl or aryl chloroformate in an anhydrous organic solvent to form the reactive mixed anhydride intermediate as the first stage of the coupling, as shown in Reaction A.

REACTION A

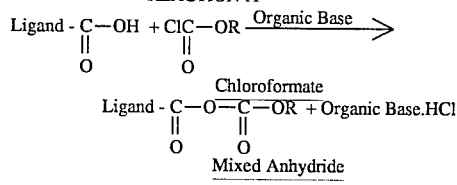

R in the chloroformate represents aryl, straight-chain or branched alkyl- or aralkyl group with 1–20 carbon atoms, preferably 1–8 carbons and more preferably 1–4 carbon atoms. Examples of commonly used chloroformates are ethyl, isobutyl, benzyl and phenyl chloroformates. Organic base, such as triethylamine, is generally included in the reaction to serve as the acceptor of the hydrochloric acid, a by-product in the formation of the mixed anhydride.

The molar ratio of ligand: choloroformate: organic base can be set at 1:1:1 or up to several-fold excess of chloroformate and organic base to ensure complete activation of the carboxylate group of the ligand. The anhydrous organic solvents used are preferably the aprotic solvents which could range from the less polar chloroform to the more polar DMF, depending on the solubility of the ligand. Mixtures of solvents, at various ratios, can also be used. (See examples in copending patent application Ser. No. 07/249,620, filed Sep. 26, 1988, abandoned in favor of file-wrapper-continuation application Ser. No. 07/871,601, filed Apr. 17, 1992, now U.S. Pat. No. 5,241,070, issued Aug. 31, 1993.)

The reaction is generally carried out at ambient temperature, but preferably at lower temperatures, down to −20 degrees C., and most preferably in an ice bath. Temperature is maintained at ambient, or preferably lower, to avoid uncontrolled exothermic or side reactions, particularly during scale-up. Temperatures between 0–15 degrees C. are commonly reported for reactions involving the use of ethyl chloroformate. Reaction time can range from a few minutes up to an hour, preferably 30 minutes after mixing all the reactants. The reaction should be worked up with a complete evaporation of all the volatiles in order to remove the excess chloroformate to prepare for the second stage of the coupling reaction. The removal of excess chloroformate (when applicable) is done to avoid complication which could arise from the undesirable reactions between the chloroformate and the functional groups of the oligonucleotide.

In the second stage of the reaction (see Reaction B), the mixed anhydride intermediate is reacted with the 3'- or 5'-end of the aminoalkyl-or mercaptoalkyl- functionalized oligonucleotide, using a mixture of an organic solvent and water as the solvent system. The organic solvent is preferentially dimethylformamide (DMF), as shown in the following reaction scheme. R' is preferably a straight chain or branched alkyl group depending on the design of the amine- or sulfhydryl- carrying modifiers, but could also contain heteroatoms and/or aryl groups.

REACTION B
3'- or 5'end

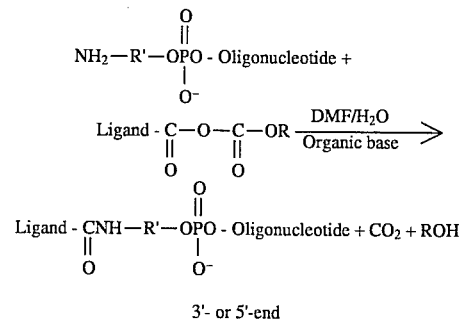

3'- or 5'-end

Various lengths of oligonucleotides and polynucleotides, these terms being used interchangeably, have been utilized in the reaction. The scheme is useful for chain lengths of up to 100 nucleotides or even longer, but preferably for chain lengths of up to 40 nucleotides.

The nucleophile-containing oligonucleotide is dissolved in aqueous medium at concentration ranging from 1 to 0.01 mM, preferably 0.1 to 0.025 mM. For example, pretreatment of the aminoalkyl-functionalized oligonucleotide solution with excess organic base, such as triethylamine at up to 100-fold molar excess, is required to ensure that the amino group of the oligonucleotide is free to react. The pretreatment is done immediately or several hours prior to mixing the oligonucleotide with the mixed anhydride intermediate. The residue containing the freshly prepared mixed anhydride intermediate is then taken up in DMF and the solution added dropwise to the oligonucleotide solution.

To maintain good solubility for all reactants, the DMF/water ratio in the final reaction mixture is generally in the range from 9:1 to 1:9, preferably 4:1 to 1:4, and more preferably around 1:1. The final volume of DMF required is generally determined such that the mixed anhydride intermediate can be dissolved in an appropriate volume of DMF and to allow the aliquoting of the desired quantity of the solution for the coupling in very small scale reaction. The mixed anhydride intermediate is generally added in the desired molar excess of 5 to less than 500-fold, preferably 10- to 200- fold, and most preferably 20- to 100- fold excess.

The coupling reaction is generally allowed to proceed, when at room temperature, for 0.5 hour to overnight. Use of lower temperature for the shortest reaction time may be necessary to improve stability of labile reactants.

The conjugate can be purified via a two-step process. The first step involves separating molecular components based on size, using, for example, gel permeation chromatography. In this step, small molecular compounds, including the ligand and its unconjugated derivatives, are separated from the macromolecular oligonucleotide.

A further separation of the unreacted oligonucleotide from the conjugate is achieved by reverse phase HPLC. Both of these chromatography techniques (gel permeation and reverse phase HPLC) are well known in the art. Due to the attachment of the more hydrophobic ligand, the conjugate is generally retained longer on the HPLC column and well-separated from the unreacted oligonucleotide. The efficiency of the conversion of the oligonucleotide to the conjugate can be determined from the HPLC system equipped with an integrator/recorder.

Many carboxylate-containing ligands that are widely used in binding assays have been found to be compatible with this mixed anhydride activation (i.e., no complicated side reactions). They can be efficiently conjugated with the amino-functionalized nucleic acids. Among this group are polysubstituted aryl acridinium esters (for example, the dimethyl ester, DMAE, described in U.S. Pat. No. 4,745,181), biotin and diacetylated-5'-carboxyfluorescein, the structures of which are shown below.

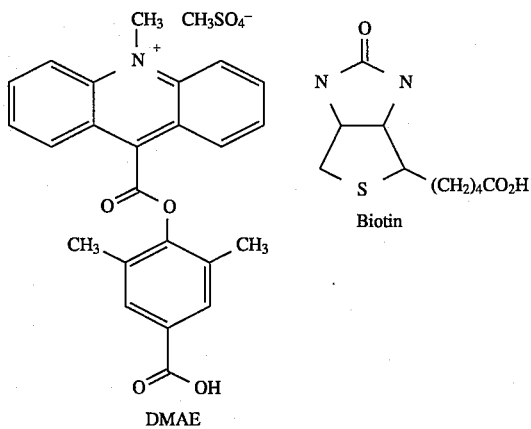
DMAE

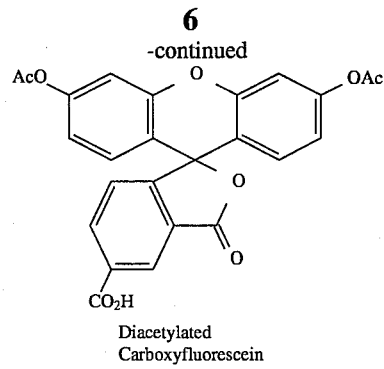
Diacetylated Carboxyfluorescein

In dealing with ligands which do not have carboxylic groups, it is necessary to derivatize them into carboxyl-carrying analogs in order to couple them to amino-functionalized polynucleotides using the methods of this invention. This technique may also be utilized when the ligands have different functional groups [for example, 2,4-dinitrofluorobenzene (DNFB) or 2,4-dinitrobenzene sulfonate (DNBS)] or when activation could result in complex/multiple products (e.g., the diazotization of arsanilic acid). Numerous methods of introducing a carboxylate group are known. For example, DNFB can be reacted with β-alanine to form 3-(2',4'-dinitrophenylamino)propionic acid (DNP-Ala) derivative with a carboxylate group attached. This ligand analog can then be made into a functional probe conjugate by the novel mixed anhydride method. Other examples for use with this coupling method include o- or p- arsanilic acid. The ligand could also be derivatized with a cyclic anhydride, such as succinic anhydride, to give the carboxylate-containing hemisuccinamido-arsanilic acid. Alternatively, a bifunctional compound carrying a carboxylate group and a phenol moiety can also be utilized to react with a diazotized arsanilic acid to form a carboxylate-containing azoarsanilic derivative. Structures of the compounds are shown below.

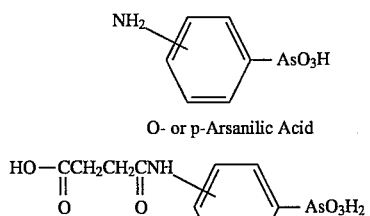
O- or p-Arsanilic Acid

Carboxylate-containing hemisuccinamido-Arsanilic Acid

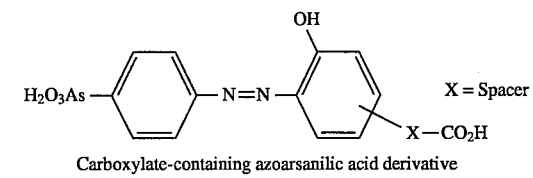
Carboxylate-containing azoarsanilic acid derivative

Probes made using this technique have been utilized in the novel hybridization assay for Campylobacter γRNA, (copending application Ser. No. 07/426,317, filed Oct. 24, 1989, abandoned in favor of file-wrapper-continuation application Ser. No. 07/816,831, filed Dec. 31, 1991, abandoned in favor of file-wrapper-continuation application Ser. No. 07/941,841, filed Sep. 8, 1992, abandoned in favor of file-wrapper-continuation application Ser. No. 08/196,815, filed Feb. 8, 1994, abandoned in favor of file-wrapper-continuation application Ser. No. 08/364,060, filed Dec. 27, 1994.) [Note, however, that the nomenclature/numbering system used for the probes in this application is different from that used in Ser. No. 07/426,387.] However, there has been no public use of these compounds, nor has their method of synthesis been previously disclosed.

The following examples describe various aspects of the preparation, purification and analysis of compounds made via the use of the instant technique. However, these examples are not intended to limit the usefulness of the newly invented techniques.

EXAMPLE 1

Label Without Carboxylate Group Derivatized into Carboxyl-Carrying Analog

Preparation of 3-(2',4'-Dinitrophenylamino) propionic acid (DNP-Ala)

To a solution of beta-alanine (1.0 g, 11.1 mmole) in 50 ml of 1M NaHCO3 was added 2,4-dinitrofluorobenzene (10.4 g, 56 mmole) in 100 ml of ethanol. The reaction mixture was stirred at room temperature for 2 hours and evaporated to remove the volatile in vacuo. The residue was transferred to a separatory funnel with water and washed twice with ethyl ether. The aqueous layer was acidified with 1N HCl until precipitation was complete. The mixture was filtered and the wet cake washed with ether. This purification process, starting from dissolving the solid in 1M NaHCO$_3$, washing the ether, and precipitating with 1N HCl, was repeated in the same manner to give yellow solid (1.6 g, 77%). e(MeOH)= 7900 (260 nm), 15900 (350 nm). NMR spectral analysis was consistent with the structure.

EXAMPLE 2

Preparation of Conjugate

General Procedure of Preparing Ligand-Nucleic Acid Conjugate by the Unconventional Mixed Anhydride Method is described below using Preparation of 5'-Biotin-Probe CJ 641.31 as an example. Probe CJ 641.31 has the sequence 5'-TCT GCC TCT CCC TCA CTC TAG ACT ATG AGT T-3'(SEQ ID NO.3).

(A) Preparation of Biotin-Mixed Anhydride (Biotin-MA) intermediate: To a solution of biotin (2 mg, 8.2 umole) (Note 1) in 2 ml of dried DMF (Aldrich, Milwaukee, Wis., Cat #22,705-6), that has been precooled in ice bath for a few minutes were added triethylamine (6.9 ul, 49 umole) and ethyl chloroformate (2.4 ul, 25 umole). The reaction mixture was stirred in ice bath for 30 minutes, treated with 2 ml of xylenes and evaporated to dryness in vacuo.

(B) Conjugation of 5'-Aminoalkyl-CJ 641.31 with Biotin-Mixed Anhydride: To a 2–4 ml vial equipped with a ⅛"×½" stirring bar was added the 5'-aminoalkyl CJ 641.31 (4 nmoles, Promega Corp. Madison, Wis.) in 200 ul of water. The solution was treated with triethylamine (400 nmoles) in about 7 ul of DMF and stirred at room temperature for 3 hours. To the residue obtained in preparation (A) that contains the activated biotin was added 1 ml of DMF. A 48.8 ul aliquot of this Biotin-MA solution containing 400 nmole equivalent of the activated Biotin was added to the CJ 641.31 solution. Another 145 ul of DMF and 400 nmoles of triethylamine in 7 ul of DMF were added immediately to the CJ 641.31 solution. The reaction mixture was then stirred at room temperature overnight.

(C) Two-step Isolation of Biotin-CJ 641.31 conjugate:

1. Gel-Permeation: The reaction mixture from Preparation (B) was passed through a Sephadex G25 (fine) column (1×40 cm) packed and eluted with water. The void volume peak monitored at 260 nm was collected, concentrated to about 0.5 ml on rotary evaporator. The collected peak was passed through another fresh Sephadex G25 column in the same manner for cleaner separation.

2. HPLC: the chromatographic conditions are the following:

Column: Aquapore C8, RP-300, 4.6 mm×25 cm (Rainin, Woburn, Mass.)
Solvent: 0.1M Et3NHOAc pH 7.2–7.4 (as Solvent A)
Acetonitrile (as solvent B)
Gradient (linear): 8% to 20% B over 20 minutes, to 40% B over 10 minutes, to 90% B over 5 minutes
Flow rate: 1 ml/min
Detection: 254 or 260 nm The probe conjugate which appeared as the major peak of retention time around 12.7 min was collected and analyzed for correct mobility and purity on the denaturing 12% polyacrylamide gel, running alongside with the oligonucleotide markers. For the purpose of visualization, all the samples analyzed on the gel electrophoresis were prelabelled enzymatically with 32P-containing phosphate or cordycepine triphosphate at 5'- or 3'- end, respectively. Autoradiography was performed after the gel was run to obtain the mobility (band) pattern of each sample on a film. This gel autorad technique is the common practice performed daily in a molecular biology lab (Ref.: Molecular Cloning: A Laboratory Manual, p. 173, 1982, T. Maniatis Ed., Cold Spring Harbor Laboratory).

Note: Biotin was used in excess for the ease of weighing. The scale of preparation (A) could be cut down proportionally as not all of the Biotin-MA was utilized in the conjugation.

EXAMPLE 3

Preparation of Probes Useful for Detecting Campylobacter

The techniques used in Example 2 were similarly used to prepare other probes, the sequence of which are shown below in the "Sequence Listing" section of this application:

Probe CJ 437.27 (SEQ ID NO. 1)
Probe CF 1107.27 (SEQ ID NO. 5)
Probe CJ 706.27 (SEQ ID NO. 4)

These three probes, in addition to the Probe CJ 641.31 described in Example 2, find usefulness in the detection of Campylobacter.

EXAMPLE 4

Preparation of Nucleic Acids and Conjugates

General Procedure of Preparing 3'-Aminoalkyl Functionalized Nucleic Acids and the 3'-Ligand-Nucleic Acid Conjugates by the Unconventional Mixed Anhydride Method is described below using Preparation of 3'-DMAE-SYOMPA 480.24 as an example. The sequence of this probe is shown below in the "Sequence Listing" section. This probe finds usefulness in the detection of Salmonella.

(A) Preparation of 3'-Aminoalkyl-SYOMPA 480.24: The synthesis of the title compound was done on an Applied Biosystem 391 DNA synthesizer using a Trityl-ON program and a 1-umole 3'-Amine-ON CPG column from Clontech Laboratories, Inc. Cleavage of the finished oligonucleotide from CPG and deprotection with ammonium hydroxide was done at room temperature for 2 hours, and then at 55 deg C. overnight. The solution was dried and the residue brought up in water, and purified by HPLC using the following conditions:

Column: Aquapore C8, RP-300, 7.0 mm×25 cm (Rainin, Woburn, Mass.)

Solvent: mixture of 0.1M Et3NHOAc pH 7.4 (as solvent A) and Acetonitrile (as solvent B).
Gradient: 8% B to 18% B over 3 minutes; stay at 18% B for 5 minutes; 18% B to 20% B over 20 minutes;
Flowrate: 2.32 ml/min
Detection: 254 nm
The major peak at 15–16 minutes containing the 5'-trityl-3'-aminoalkyl-SA24 was collected, evaporated, and brought up in 600 ul of water. Detritylation was done by treating the solution with n equal volume of 2% Trifluoroacetic acid at room temperature for 8 minutes, followed by neutralization with 600 ul of 10-fold diluted NH4OH concentrate. The reaction mixture was dried on rotary evaporator. The residue was brought up in water, and purified by HPLC using the following conditions:
Column: same as above
Solvent: same as above
Gradient: 5% B to 13% B over 20 minutes; 13% B to 40% B over 5 minutes; 40% B to 60% B over 5 minutes.
Flowrate: same as above
Detection: same as above
The major peak at 20–21 minutes was collected, evaporated and repurified by HPLC using the following conditions:
Column: same as above
Solvent: same as above
Gradient: 5% B to 15% B over 50 minutes
Flowrate: same as above
Detection: same as above
The major peak at 34–35 minutes was collected, dried and brought up in water.

(B) Conjugation of 3'-Aminoalkyl-SYOMPA 480.24 with DMAE-Mixed Anhydride: The 3'-Aminoalkyl-SYOMPA 480.24 was pretreated with 100 molar excess of triethylamine for 3 hours at room temperature. The DMAE-Mixed Anhydride was prepared in the same manner as described for Biotin-Mixed Anhydride in Example 2, Section (A). The coupling was set up in 150 ul each of dimethylformamide and water, with a 100 molar excess of DMAE-Mixed Anhydride, as well as an additional similar amount of triethylamine. The reaction mixture was stirred at room temperature overnight, put through a Sephadex G25 column, eluted with water. The first peak was collected and concentrated on a rotary evaporator. The concentrate was further purified by HPLC using the following conditions:
Column: Aquapore C8, RP-300, 7.0 mm×25 cm (Rainin, Woburn, Mass.)
Solvent: Mixture of 0.1M Et3NHOAc, pH 7.4 (as solvent A) and Acetonitrile (as solvent B)
Gradient: 8% B to 20% B over 20 minutes; 20% B to 40% B over 10 minutes; 40% to 60% B over 10 minutes
Flowrate: 2.32 ml/min
Detection: 254 nm
A peak at 21 minutes as the desired product was collected and dried. The residue was brought up in 400 ul of water, and a small aliquot of the probe conjugate solution was analyzed as described in Example 2.

EXAMPLE 5

Optimization of Reaction

An experiment to evaluate the effect of different chemical species used to activate the ligand and the reactivity of the different terminal groups on the polynucleotide was conducted. (See Table 1.) The study of reaction of various activated dimethyl acridinium esters (DMAE) with polynucleotides showed that the polynucleotide with the terminal 5'-hydroxy group (5'-OH-PM1) did not react significantly with the mixed anhydride intermediate, indicating that side reactions with purine or pyrimidine groups of the oligonucleotide are minimal. Furthermore, DMAE activated with N-hydroxysuccinimide (DMAE-NHS) does not significantly react with the polynucleotide at low loading ratio of 20:1.

TABLE 1

| DMAE LABELLING EFFICIENCY FOR POLYLINKER PM1 | | | |
| --- | --- | --- | --- |
| REACTANTS | | MOLAR REACTION RATIO | LABELLING EFFICIENCY |
| 1. DMAE-NHS | NH2-PM1 | 20:1 | 7.8% |
| 2. DMAE-MA | NH2-PM1 | 20:1 | 65% |
| 3. DMAE-MA | NH2-PM1 | 40:1 | 70% |
| 4. DMAE-MA | 5'-OH-PM1 | 20:1 | 2% |

What is claimed is:

1. A method for conjugating a label to aminoalkyl-functionalized single-stranded polynucleotides comprising:
  a. forming a mixed anhydride intermediate containing said label by reacting a carboxylate-containing ligand with chloroformate in the presence of an anhydrous aprotic organic solvent,
  b. evaporating the chloroformate and other volatile components, and
  c. reacting said intermediate, redissolved in an anhydrous aprotic organic solvent system, with said polynucleotide dissolved in water, such that the ratio of the aprotic organic solvent system portion to the water portion ranges from about 9:1 to 1:9, wherein said label is capable of forming said mixed anhydride intermediate and said chloroformate is of the structure ROC(O)Cl, where R represents aryl, straight chain or branched alkyl- or aralkyl group with up to 20 carbon atoms.

2. A method of claim 1 in which the aprotic solvent is dimethylformamide.

3. A method of claim 1 wherein the label comprise haptens, ligands or luminescent labels.

4. A method of claim 1 wherein the formation of the intermediate comprises reacting a label with chloroformate in the presence of organic base.

5. A method of claim 1 wherein the R group contains up to 8 carbon atoms.

6. A method of claim 5 wherein the R group contains up to 4 carbon atoms.

7. A method of claim 4 wherein the organic base is triethylamine.

8. A method of claim 1 in which the polynucleotide has a reactive amine at its 3'- or 5'- end.

9. A method of claim 1 in which the ratio is between 4:1 and 1:4.

10. A method of claim 9 in which the ratio is approximately 1:1.

11. A method of claim 1 in which the polynucleotide contains up to 100 nucleotides.

12. A method of claim 11 in which the polynucleotide contains up to 40 nucleotides.

13. A method of claim 1 wherein the polynucleotide is a gene probe.

14. A gene probe for use in an assay for detection of Campylobacter 16s rRNA gene, where said gene probe is made by the method of claim 26 and said gene probe is selected from the group consisting of SEQ ID NO. 1, SEQ ID NO. 3, SEQ ID NO. 4, and SEQ ID NO. 5.

15. A method of claim 1 in which said aprotic organic solvent system contains more than 1 solvent.

16. A method for conjugating haptens, ligands or luminescent labels to aminoalkyl functionalized single-stranded polynucleotides comprising:
  a. forming a mixed anhydride intermediate containing said hapten, ligand or luminescent label by reacting a carboxylate-containing hapten, ligand or luminescent label with chloroformate in the presence of an anhydrous aprotic organic solvent, b. evaporating the chloroformate and other volatile components, and c. reacting said intermediate, redissolved in an anhydrous aprotic organic solvent system, with said polynucleotide dissolved in water, such that the ratio of the aprotic organic solvent system portion to the water portion ranges from about 9:1 to 1:9, wherein said label is capable of forming said mixed anhydride intermediate and said chloroformate is of the structure ROC(O)Cl, where R represents aryl, straight chain or branched alkyl- or aralkyl group with up to 20 carbon atoms.

17. A method of claim 16 in which the aprotic solvent is dimethylformamide.

18. A method of claim 16 wherein the R group contains up to 8 carbon atoms.

19. A method of claim 18 wherein the R group contains up to 4 carbon atoms.

20. A method of claim 16 in which the polynucleotide contains up to 100 nucleotides.

* * * * *